US00PP32839P2

(12) United States Plant Patent
Laughner

(10) Patent No.: US PP32,839 P2
(45) Date of Patent: Feb. 23, 2021

(54) ***OSTEOSPERMUM* PLANT NAMED 'SUNSHINE BEAUTY'**

(50) Latin Name: *Osteospermum ecklonis*
Varietal Denomination: Sunshine Beauty

(71) Applicant: Ball Horticultural Company, West Chicago, IL (US)

(72) Inventor: Linda Laughner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/879,487

(22) Filed: May 20, 2020

(51) Int. Cl.
*A01H 6/14* (2018.01)
*A01H 5/02* (2018.01)

(52) U.S. Cl.
USPC ..... Plt./360

(58) Field of Classification Search
USPC ..... Plt./360
See application file for complete search history.

*Primary Examiner* — Annette H Para
(74) *Attorney, Agent, or Firm* — Audrey Charles

(57) ABSTRACT

A new and distinct cultivar of *Osteospermum* plant named 'Sunshine Beauty', characterized by its deep orange-yellow and yellow colored inflorescences, medium green-colored foliage, and moderately vigorous, upright-mounded growth habit, is disclosed.

1 Drawing Sheet

Latin name of genus and species of plant claimed: *Osteospermum ecklonis.*

Variety denomination: 'Sunshine Beauty'.

BACKGROUND OF THE INVENTION

The present invention relates to a new and distinct cultivar of *Osteospermum* plant botanically known as *Osteospermum ecklonis* and hereinafter referred to by the cultivar name 'Sunshine Beauty'.

The new cultivar originated in a controlled breeding program in Santa Paula, Calif. during February 2015. The objective of the breeding program was the development of *Osteospermum* cultivars that are freely flowering with unique flower coloration and a freely branching, upright-mounded growth habit.

The new *Osteospermum* cultivar is the result of cross-pollination. The female (seed) parent of the new cultivar is the proprietary *Osteospermum ecklonis* breeding selection coded 84820-3, not patented, characterized by its dark yellow-orange colored inflorescences, medium green-colored foliage, and moderately vigorous, upright-mounded growth habit. The male (pollen) parent of the new cultivar is the proprietary. *Osteospermum ecklonis* breeding selection coded 58876-3, not patented, characterized by its dark yellow-orange colored inflorescences, medium green-colored foliage, low to moderate growth vigor, and upright-mounded growth habit. The new cultivar was selected as a single flowering plant within the progeny of the above stated cross-pollination during February 2016 in a controlled environment in Santa Paula, Calif.

Asexual reproduction of the new cultivar by terminal stern cuttings since February 2016 in Santa. Paula, Calif. and Arroyo Grande Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Sunshine Beauty' as a new and distinct cultivar of *Osteospermum* plant:

1. Deep orange-yellow and yellow colored inflorescences;
2. Medium green-colored foliage; and
3. Moderately vigorous, upright-mounded growth habit.

Plants of the new cultivar differ from plants of the female parent primarily in having inflorescences with a larger diameter. Plants of the new cultivar differ from plants of the male parent primarily in having inflorescences with a larger diameter and increased growth vigor.

Of the many commercially available *Osteospermum* cultivars, the most similar in comparison to the new cultivar is Blue Eyed Beauty 'Balostlueye', U.S. Plant Pat. No. 26,150. However, in side-by-side comparison, plants of the new cultivar differ from plants of 'Balostlueye' in at least the following characteristics:

1. Plants of the new cultivar have a ray floret color that does not have a large red-purple colored area like plants of 'Balostlueye';
2, Plants of the new cultivar have smaller diameter inflorescences than plants of 'Balostlueye'; and
3. Plants of the new cultivar have shorter disc florets than plants of 'Balostlueye'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Sunshine Beauty'. The approximately 4-month-old plants and were grown in 4.5-inch pots for 12 weeks in a greenhouse in West Chicago, Ill. Plants were given one pinch two weeks before transplant.

DETAILED BOTANICAL DESCRIPTION

Figure 1:
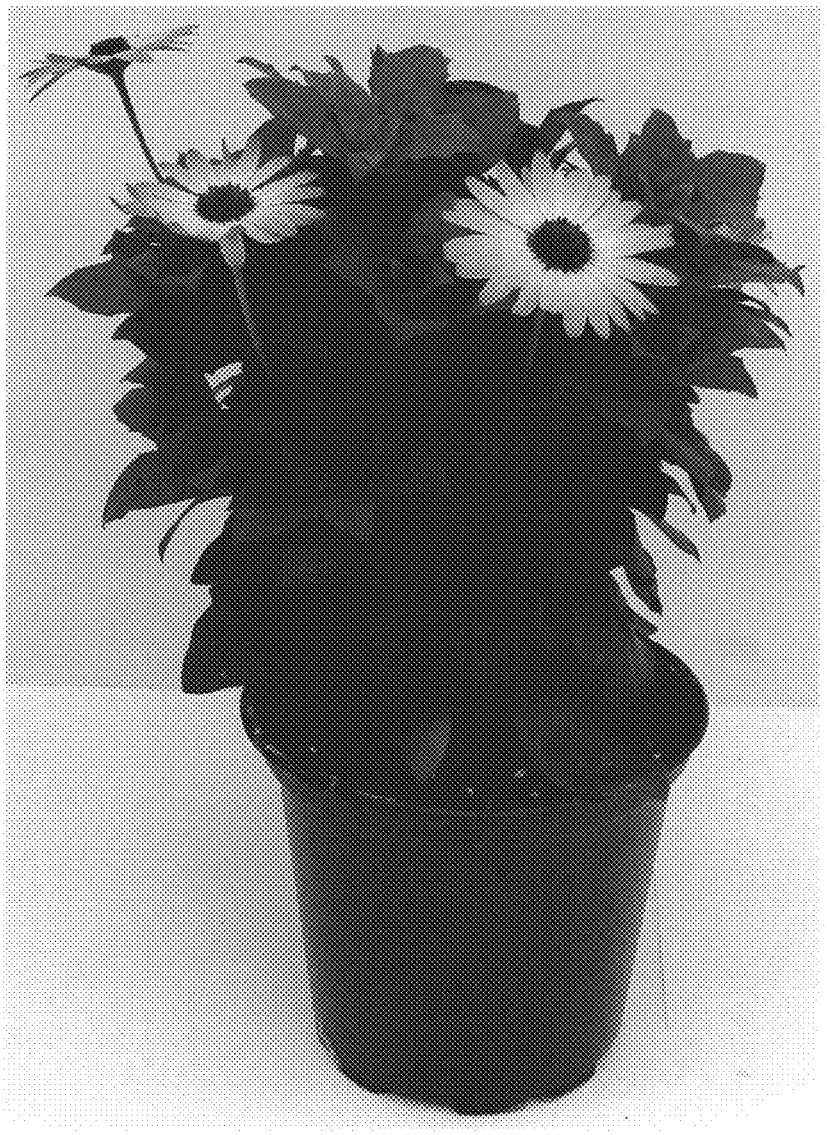
FIG. 1 illustrates a side view of the overall growth and flowering habit of 'Sunshine Beauty'.
Figure 2:
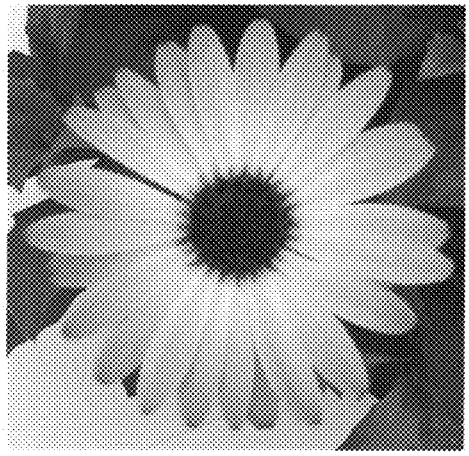
FIG. 2 illustrates a close-up view of an individual inflorescence of 'Sunshine Beauty'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in January 2020 under natural light conditions in West Chicago, Ill.

The following descriptions and measurements describe approximately 4-month-old plants produced from cuttings from stock plants and grown in a glass-covered greenhouse under conditions comparable to those used in commercial practice. The plants were grown in West Chicago, Ill. in 4.5-inch pots for 12 weeks utilizing a soilless growth medium. Plants were given one pinch two weeks before transplant. Greenhouse temperatures were maintained at approximately 67° F. to 72° F. (19° C. to 22° C.) during the day and approximately 64° F. to 66° F. (18° C. to 19° C.) during the night. Supplemental lighting was used. Measurements and numerical values represent averages of typical plants.

Botanical classification: *Osteospermum ecklonis* 'Sunshine Beauty'.

Parentage:

*Female parent*.—Proprietary *Osteospermum ecklonis* breeding selection coded 84820-3, not patented.

*Male parent*.—Proprietary *Osteospermum ecklonis* breeding selection coded 58876-3, not patented.

Propagation:

*Type cutting*.—Terminal stem.

*Time to initiate roots*.—Approximately 9 to 12 days.

*Time to produce a rooted cutting*.—Approximately 21 to 28 days.

*Root description*.—Fibrous.

*Rooting habit*.—Freely branching.

Plant description:

*Commercial crop time*.—Approximately 10 to 13 weeks from a rooted cutting to finish in a 10 cm pot.

*Growth habit and general appearance*.—Moderately vigorous, upright-mounded.

*Size*.—Height from soil level to top of plant plane: Approximately 16.5 cm. Width: Approximately 22.0 cm.

*Branching habit*.—Freely branching, pinching enhances basal branching. Quantity of main branches per plant: Approximately 10.

*Branch*.—Strength: Strong. Length to base of peduncle: Approximately 11.0 cm. Diameter: Approximately 4.0 mm. Length of central internode: Approximately 5.0 mm. Texture: Glabrous. Color of young and mature stems: 145B to 145A.

Foliage description:

*General description*.—Quantity of leaves per main branch: Approximately 16. Fragrance: Moderate. Form: Simple. Arrangement: Alternate.

*Leaves*.—Aspect: Acute angle to stem becoming an obtuse angle with age. Shape: Spatulate. Margin: Widely dentate. Apex: Acute to broadly acute. Base: Attenuate. Venation pattern: Pinnate. Length of mature leaf: Approximately 4.5 cm. Width of mature leaf: Approximately 2.5 cm. Texture of upper and lower surfaces: Sparsely pubescent, densely pubescent on margins. Color of upper surface of young and mature foliage: 137A with venation of 146C to indistinguishable. Color of lower surface of young and mature foliage: Closest to 138A with venation of 146C to indistinguishable.

*Petiole*.—Length: Approximately 1.2 cm. Diameter: Approximately 4.0 mm. Texture: Densely pubescent on flattened edges. Color: 146C.

Flowering description:

*Flowering habit*.—'Sunshine Beauty' is freely flowering under outdoor growing conditions with substantially continuous blooming from spring through autumn and year-round in greenhouse environment.

*Lastingness of individual inflorescence on the plant*.—Approximately 8 to 10 days.

Inflorescence description:

*General description*.—Type: Solitary, composite. Persistent. Shape: Round. Aspect: Facing upward. Arrangement: Terminal, held above the foliage, arising from leaf axils. Disc and ray florets develop acropetally on a capitulum. Fragrance: Faint. Quantity per plant: Approximately 4. Diameter: Approximately 5.5 cm. Depth: Approximately 1.1 cm.

*Peduncle*.—Strength: Strong. Aspect: Erect. Length: Approximately 10.5 cm. Diameter: Approximately 2.0 mm. Texture: Glandular pubescent. Gland color: Colorless. Color: 144A.

*Bud*.—Rate of opening: Generally takes 4 to 6 days for bud to progress from first color to fully open flower. Quantity per plant: Approximately 2.

*Bud just before opening*.—Shape: Ovoid. Length: Approximately 1.1 cm. Diameter: Approximately 1.2 cm. Color: 154D.

*Ray florets*.—Quantity per inflorescence: Approximately 26. Arrangement: Imbricate in a single whorl. Aspect: Initially at acute angle to disc, becoming perpendicular at maturity and downward turning as senesce. Shape: Oblanceolate. Margin: Entire. Apex: Emarginate with three tips. Base: Attenuate. Length: Approximately 2.5 cm. Width: Approximately 6.0 mm. Texture of upper surface: Glabrous, ribbed longitudinally. Texture of lower surface: Glabrous with a densely pubescent base, ribbed longitudinally. Color of upper surface when first open: N163D with 163A at apex transitioning at center to 8B through 8D at base, small overlay of 77A at base. Color of lower surface when first and fully open: 162D. Color of upper surface when fully open: 163A at apex transitioning at center to 8B through 8D at base, small overlay of 77A at base.

*Disc florets*.—Quantity per inflorescence: Approximately 115. Arrangement: Massed in center of inflorescence. Shape: Tubular. Margin: Entire. Apex: Five to six acute tips. Base: Fused. Length: Approximately 7.0 mm. Diameter at apex: Approximately 2.0 mm. Diameter at base: Approximately 1.0 mm. Texture: Glabrous with a sparsely pubescent outer surface. Color when fully open: Closest to N155D with a heavy overlay of 77D, tips of N92A, base of 145D.

*Disc*.—Diameter: Approximately 1.2 cm. Depth: Approximately 6.0 mm.

*Receptacle*.—Shape: Conical. Height: Approximately 3.0 mm. Diameter: Approximately 4.0 mm. Color: 155D.

*Phyllaries*.—Quantity per inflorescence Approximately 26. Arrangement: Imbricate, in a single whorl. Shape: Linear to lanceolate. Margin: Entire. Apex: Acute. Base: Truncate. Length: Approximately 1.1 cm. Width: Approximately 1.0 mm to 2.0 mm. Texture of upper or inner surface: Glabrous. Texture of lower or outer surface: Mixture of glandular and non-glandular pubescence. Gland color: Colorless, transparent. Color of upper or inner surface: 138B. Color of lower or outer surface: 138A.

*Reproductive organs*.—Androecium: Present on disc florets only. Stamen quantity: 5 per floret, fused around the style. Stamen length: Approximately 4.0 mm. Anther shape: Linear. Anther length: Approximately 2.0 mm. Anther color: N186A. Pollen amount: Abundant. Pollen color: 23A. Gynoecium: Present on ray and disc florets. Pistil quantity: 1 per floret. Pistil length: Approximately 7.0 mm. Stigma shape: Two thick lobes positioned closely together, appearing rounded. Stigma length: Less than 1 mm. Stigma color: N92B. Style length: Approximately 5.0 mm. Style color: 155D. Ovary length: Approximately 2.0 mm. Ovary color: 145D.

Seed and fruit production: Neither seed nor fruit production has been observed.

Disease and pest resistance: Resistance to pathogens and pests common to *Osteospermum* has not been observed.

What is claimed is:

1. A new and distinct cultivar of *Osteospermum* plant named 'Sunshine Beauty', substantially as herein illustrated and described.

* * * * *